United States Patent
Kishi

(10) Patent No.: US 8,818,560 B2
(45) Date of Patent: Aug. 26, 2014

(54) MASTER-SLAVE MANIPULATOR

(75) Inventor: Kosuke Kishi, Hachioji (JP)

(73) Assignee: Olympus Corporation, Tokyo (JP)

( * ) Notice: Subject to any disclaimer, the term of this patent is extended or adjusted under 35 U.S.C. 154(b) by 652 days.

(21) Appl. No.: 13/074,667

(22) Filed: Mar. 29, 2011

(65) Prior Publication Data

US 2012/0059519 A1 Mar. 8, 2012

(30) Foreign Application Priority Data

Sep. 7, 2010 (JP) ................................ 2010-200248

(51) Int. Cl.
- *G05B 19/04* (2006.01)
- *G05B 19/18* (2006.01)
- *G05B 15/00* (2006.01)
- *G05B 19/00* (2006.01)

(52) U.S. Cl.
USPC ........... 700/262; 700/251; 700/254; 700/257; 700/264; 901/14; 901/15; 901/16; 901/27; 901/28; 901/29

(58) Field of Classification Search
CPC ................... A61B 19/2203; A61B 2019/2223; A61B 2019/2269; A61B 2019/5248; A61B 2019/2276; A61B 19/22; A61B 2017/00703; A61B 2019/223; A61B 2019/2234; A61B 2017/00477; A61B 2019/2246; A61B 2019/2292; A61B 2019/2296; A61B 2019/265; B25J 13/02; B25J 3/04; B25J 9/1689; B25J 3/00; B25J 9/1615
See application file for complete search history.

(56) References Cited

U.S. PATENT DOCUMENTS

| | | | | |
|---|---|---|---|---|
| 4,975,856 A | * | 12/1990 | Vold et al. | 700/263 |
| 5,737,500 A | * | 4/1998 | Seraji et al. | 700/251 |
| 6,889,117 B2 | * | 5/2005 | Sabe et al. | 700/245 |
| 8,489,235 B2 | * | 7/2013 | Moll et al. | 700/245 |
| 2002/0120363 A1 | | 8/2002 | Salisbury et al. | |
| 2005/0043718 A1 | * | 2/2005 | Madhani et al. | 606/1 |

(Continued)

FOREIGN PATENT DOCUMENTS

| | | |
|---|---|---|
| JP | 63-118804 | 5/1988 |
| JP | 63-267177 | 11/1988 |

(Continued)

OTHER PUBLICATIONS

ApproximationOfJacobianInverse.pdf (Krzysztof Tchon' , Joanna Karpin' Ska, Mariusz Janiak, Approximation of Jacobian Inverse Kinematics Algorithms, 2009, Int. J. Appl. Math. Comput. Sci., vol. 19, No. 4, 519-531).*

(Continued)

*Primary Examiner* — Khoi Tran
*Assistant Examiner* — Bao Long T Nguyen
(74) *Attorney, Agent, or Firm* — Scully, Scott, Murphy & Presser, P.C.

(57) ABSTRACT

A master-slave manipulator includes a remote manipulation device, a slave manipulator, and a control unit. The remote manipulation device as a master gives an operating command corresponding to a plurality of degrees of freedom. The slave manipulator includes a plurality of joints corresponding to the degrees of freedom. The slave manipulator includes a redundant joint among the joints. The control unit controls operations of the joints in accordance with the operating command. The control unit calculates an orientation change of the remote manipulation device from the operating command at predetermined time intervals and selects and drives one of the joints in redundancy relationship among the joints in accordance with the orientation change.

13 Claims, 7 Drawing Sheets

(56) References Cited

U.S. PATENT DOCUMENTS

| | | | |
|---|---|---|---|
| 2007/0013336 A1 | 1/2007 | Nowlin et al. | |
| 2008/0071291 A1* | 3/2008 | Duval et al. | 606/130 |
| 2008/0161677 A1* | 7/2008 | Sutherland et al. | 600/417 |
| 2008/0202274 A1* | 8/2008 | Stuart | 74/490.02 |
| 2010/0063630 A1* | 3/2010 | Sutherland et al. | 700/264 |
| 2010/0275718 A1* | 11/2010 | Stuart et al. | 74/490.01 |
| 2011/0270271 A1* | 11/2011 | Nowlin et al. | 606/130 |
| 2011/0282359 A1* | 11/2011 | Duval | 606/130 |

FOREIGN PATENT DOCUMENTS

| | | |
|---|---|---|
| JP | 64-16389 | 1/1989 |
| JP | 64-20983 | 1/1989 |
| JP | 05-228854 | 9/1993 |
| JP | 05-285863 | 11/1993 |
| JP | 05-301180 | 11/1993 |
| JP | 2003-340752 | 12/2003 |
| JP | 2005-014156 | 1/2005 |
| JP | 2005-193311 | 7/2005 |
| WO | 00/30548 A1 | 6/2000 |
| WO | 00/60521 A1 | 10/2000 |
| WO | WO 2008/103425 A1 | 8/2008 |

OTHER PUBLICATIONS

64016389JPA.tran.pdf (English translation of JP 64016389, Phoenix Translation, Oct. 2013, PTO, pp. 1-18)).*

International Preliminary Report on Patentability together with the Written Opinion dated Apr. 18, 2013 received in related International Application No. PCT/JP2011/070213.

International Search Report PCT/JP2011/070213 dated Nov. 8, 2011, together with an English language translation.

Communication Pursuant to Article 94(3) EPC dated May 16, 2014 in counterpart European Patent Application No. 11 823 547.2.

* cited by examiner

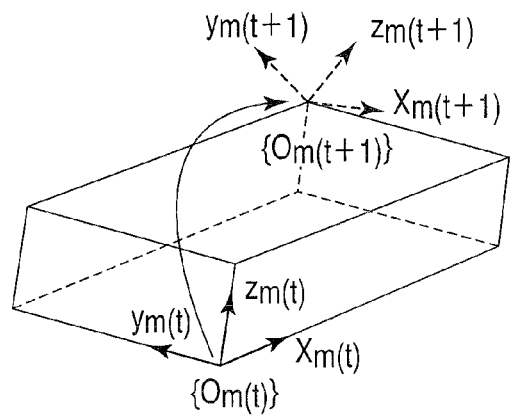
F I G. 4A
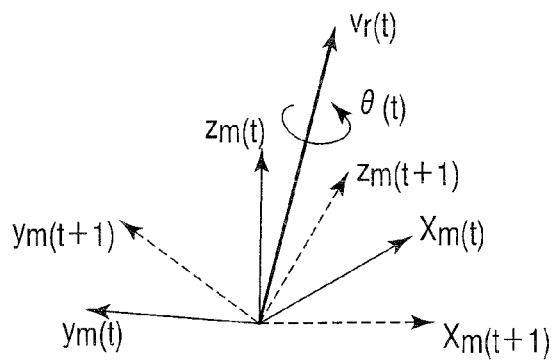
F I G. 4B
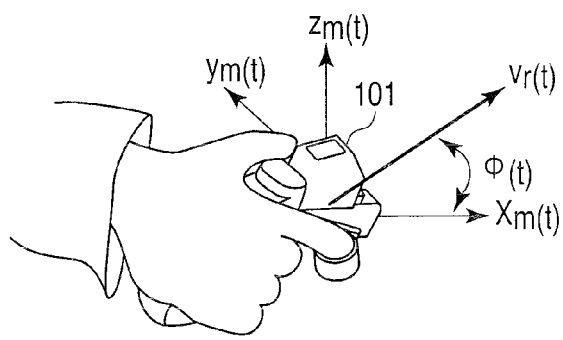
F I G. 4C

MASTER-SLAVE MANIPULATOR

CROSS-REFERENCE TO RELATED APPLICATIONS

This application is based upon and claims the benefit of priority from prior Japanese Patent Application No. 2010-200248, filed Sep. 7, 2010, the entire contents of which are incorporated herein by reference.

BACKGROUND OF THE INVENTION

1. Field of the Invention

The invention relates to a master-slave manipulator including a redundant joint.

2. Description of the Related Art

In order to attain labor reduction in medical care facilities, medical treatments to be performed by robots have recently been studied. Particularly, in the field of surgery, various proposals have been made on a manipulator system with which treatment on a patient is performed by using a manipulator including a multiple degree of freedom (multiple joint) arm. Among the manipulator systems, a master-slave manipulator in which a slave manipulator brought into direct contact with a body cavity of a patient is remote-manipulated by a remote manipulation device is known.

In the case where a suturing motion which is especially difficult in endoscopic surgery is performed by using the master-slave manipulator, a gripper attached to a leading end of a slave arm is rolled for the suturing. In this case, when the slave arm is not provided with a roll axis joint at the leading end, other joints are caused to operate in cooperation with a rolling operation for rolling the gripper attached to the leading end. In this case, there is a possibility that a multiple of joints are operated to collide with a circumjacent organ or the like. As a countermeasure, Jpn. Pat. Appln. KOKAI Publication No. 63-267177, for example, proposes a master-slave manipulator in which positioning and posturing only of the leading end is enabled by a redundant joint provided at a leading end portion.

BRIEF SUMMARY OF THE INVENTION

According to an aspect of the invention, there is provided a master-slave manipulator comprising: a remote manipulation device as a master which gives an operating command corresponding to a plurality of degrees of freedom; a slave manipulator which includes a plurality of joints corresponding to the degrees of freedom and includes a redundant joint among the joints; and a control unit which controls operations of the joints in accordance with the operating command, wherein the control unit calculates an orientation change of the remote manipulation device from the operating command at predetermined time intervals and selects and drives one of the joints in redundancy relationship among the joints in accordance with the orientation change.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 4A, 4B, and 4C are diagrams illustrating a concept for joint selection according to the embodiment of the invention;

DETAILED DESCRIPTION OF THE INVENTION

Hereinafter, an embodiment of the invention will be described with reference to the accompanying drawings.

Figure 1:
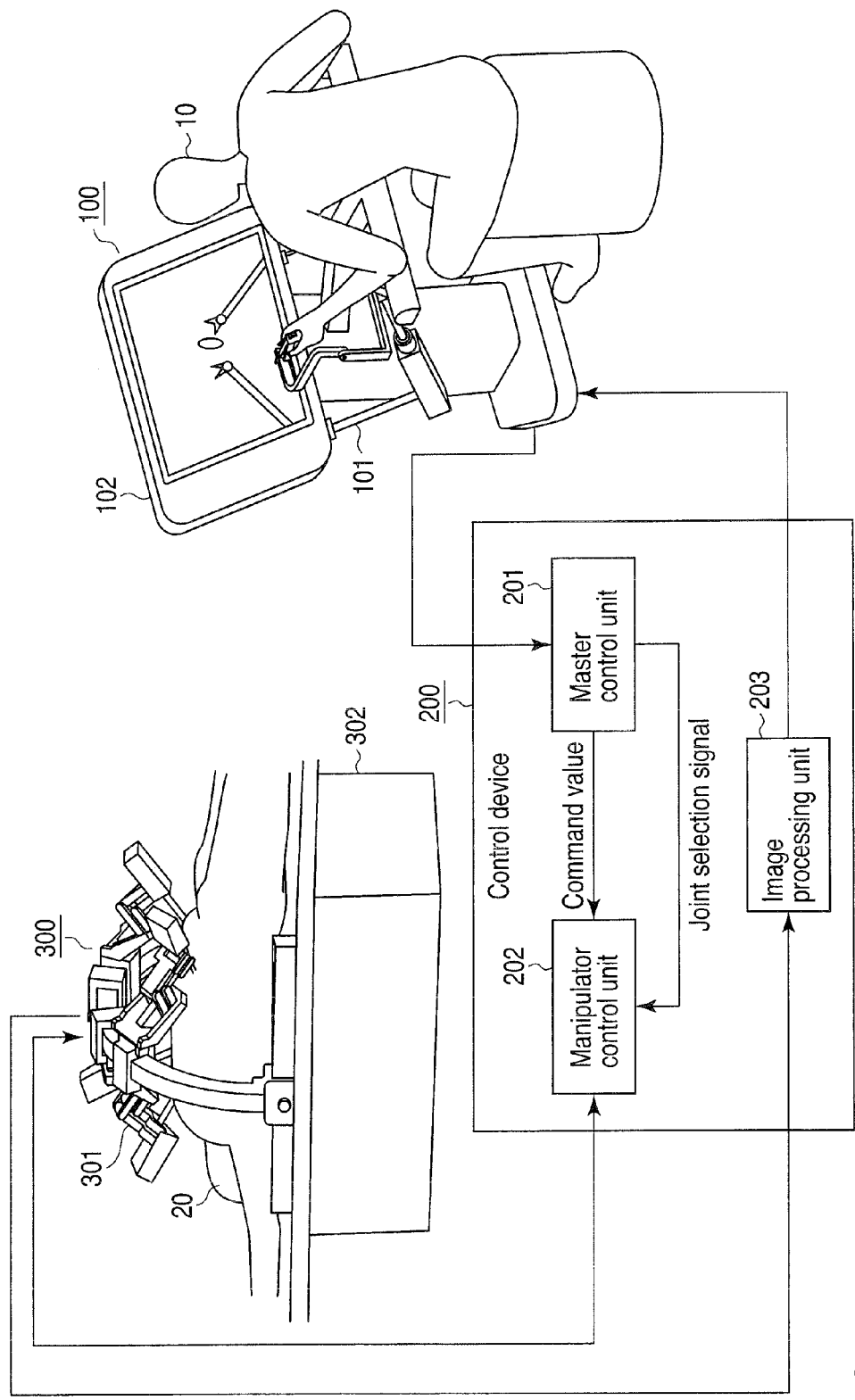
FIG. 1 is a diagram showing an overall configuration of a master-slave manipulator according to an embodiment of the invention.

FIG. 1 is a diagram showing an overall configuration of a master-slave manipulator according to an embodiment of the invention. As shown in FIG. 1, a master-slave manipulator according to the embodiment includes a remote manipulation device 100, a control device 200, and a slave manipulator 300. Shown in FIG. 1 is an application example of the master-slave manipulator of the embodiment to a medical usage. However, the master-slave manipulator of the embodiment is applicable to various usages other than the medical usage.

The remote manipulation device 100 functions as a master in the master-slave manipulator. The remote manipulation device 100 includes a manipulation unit 101 and a display unit 102.

Figure 2A:
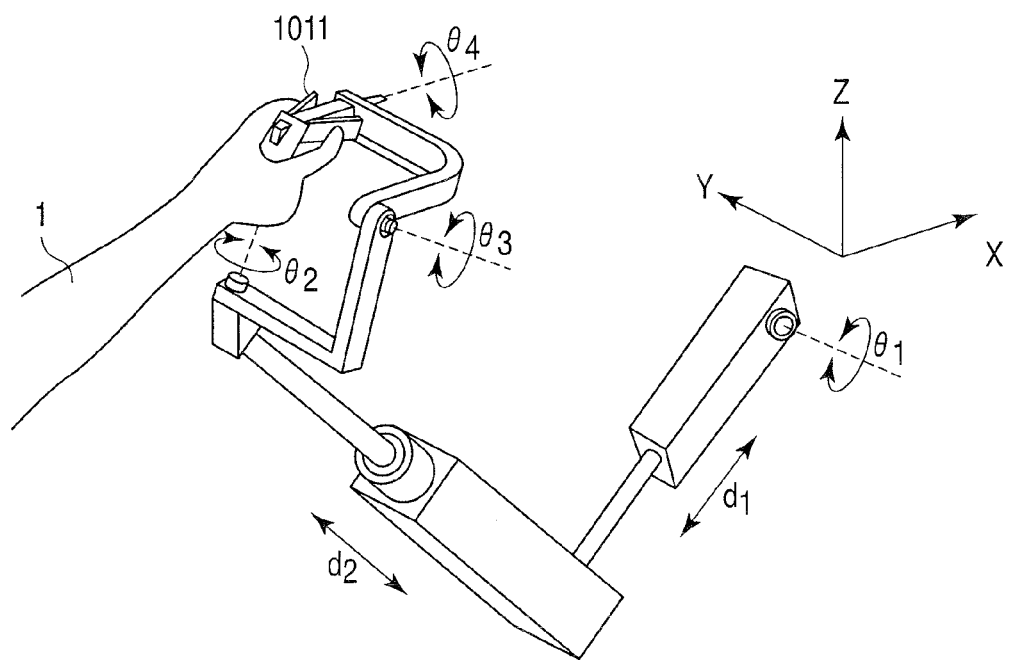
FIGS. 2A and 2B are diagrams showing an example of a configuration of a remote manipulation device.

For example, the manipulation unit 101 includes a driving unit including a driven axis formed of a rotation mechanism and a driven axis formed of a linear motion mechanism as shown in FIG. 2A. Further, a gripper unit 1011 is provided at a rear end portion of the manipulation unit 101. The rear end portion of the manipulation unit 101 is a side gripped by an operator 10. With such configuration, the driven axes forming the manipulation unit 101 are driven when the operator 10 moves or rotates the manipulation unit 101 or operates the gripper unit 1011 in a state of gripping the gripper unit 1011. A driving amount of each driven axis is detected by a position detector (encoder, for example) (not shown) provided in each of the driven axes. As to the driving amounts of the driven axes, the driving amount is a rotation angle in the case where the driven axis is the rotation mechanism, and the driving amount is a displacement amount in the case where the driven axis is the linear motion mechanism. A detection signal from each of the detectors is output to the control device 200 as a signal (manipulation signal) indicating an operating command of the manipulation unit 101 for instructing a position and an orientation of the leading end of a slave arm 301 of the slave manipulator 300. Referring to FIG. 2A, the manipulation unit 101 is provided with six driven axes, and outputs manipulation signals corresponding to 6 degrees of freedom for calculating six command values by driving of the six driven axes. The manipulation signals include signals ($\theta_1$, $d_1$, $d_2$) relating to the position and signals ($\theta_2$, $\theta_3$, $\theta_4$) relating to the orientation.

Figure 2B:
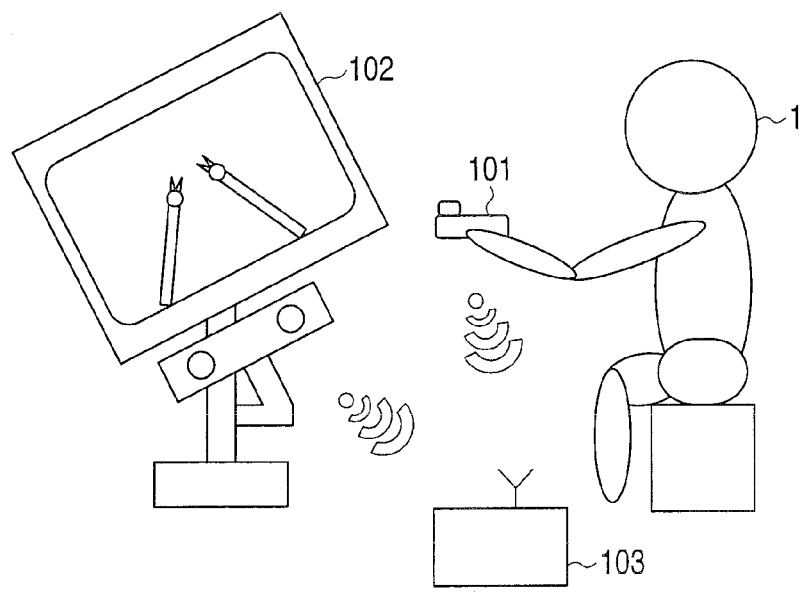

The configuration of the manipulation unit 101 is not particularly limited as long as the manipulation unit is capable of instructing a position and an orientation of the leading end of the slave arm 301. For example, sensors (acceleration sensors, for example) which detect translation of horizontal three axes and sensors (angular velocity sensors, for example) which detect rotations about the axes may be provided in the manipulation unit 101. In this case, the manipulation unit 101 may be of a handheld type as shown in FIG. 2B, for example. In the example of FIG. 2B, the operator 10 moves or rotates the handheld manipulation unit 101 in a three-dimensional space to give manipulation signals corresponding to 6 degrees of freedom. Shown in FIG. 2B is one example of wireless communication of the manipulation signals obtained by the manipulation unit 101 via a wireless communication unit 103. Of course, wired communication of the manipulation signals obtained by the manipulation unit 101 may be applied to the example of FIG. 2B.

The display unit 102 is formed of a liquid crystal display, for example, and displays an image based on an image signal input from the control device 200. As described later in this specification, the image signal input from the control device 200 is obtained by subjecting an image signal obtained via an electronic camera (electronic endoscope) attached to the slave arm 301 to a processing by the control device 200. Since the image based on the image signal is displayed on the display unit 102, it is possible for the operator 10 of the remote manipulation device 100 to confirm the image of the leading end of the slave manipulator 300 disposed at a place distant from the remote manipulation device 100.

The control device 200 serving as a controller includes a master control unit 201, a manipulator control unit 202, and an image processing unit 203.

The master control unit 201 calculates command values of a position and an orientation of the leading end of the slave arm 301 by kinematic calculation in accordance with the manipulation signals corresponding to the 6 degrees of freedom from the remote manipulation device 100. The master control unit 201 selects one of joints in redundancy relationship among joints of the slave arm 301 as a driven joint in accordance with the manipulation signals from the remote manipulation device 100. The master control unit 21 outputs a joint selection signal indicating a result of the selection together with the command values of the position and the orientation to the manipulator control unit 202.

As used herein, the term "in redundancy relationship" means a relationship in which rotation axes of joints are parallel to each another.

Upon reception of the command values of position and orientation and the joint selection signal from the remote manipulation device 100, the manipulator control unit 202 calculates driving amounts of the joints of the slave arm 301 by an inverse kinematic calculation in order to match the position and the orientation of the leading end of the slave arm 301 to the command values. The slave arm 301 according to the embodiment includes joints corresponding to 7 degrees of freedom as described later in this specification, and each of joints is driven by using one of the joints as a fixed joint. Therefore, since it is possible to reduce the number of joints to be calculated by the inverse kinematic calculation as compared to the case in which all of driving amounts of 7 degrees of freedom are unknown, it is possible to simplify the inverse kinematic calculation.

The image processing unit 203 processes the image signal obtained by the electronic camera (electronic endoscope or the like) provided at the leading end of the slave arm 301 to generate the image signal to be displayed on the display unit 102. After that, the image processing unit 203 outputs the generated image signal to the display unit 102.

The slave manipulator 300 includes the slave arm 301 and a surgical table 302.

Figure 3:
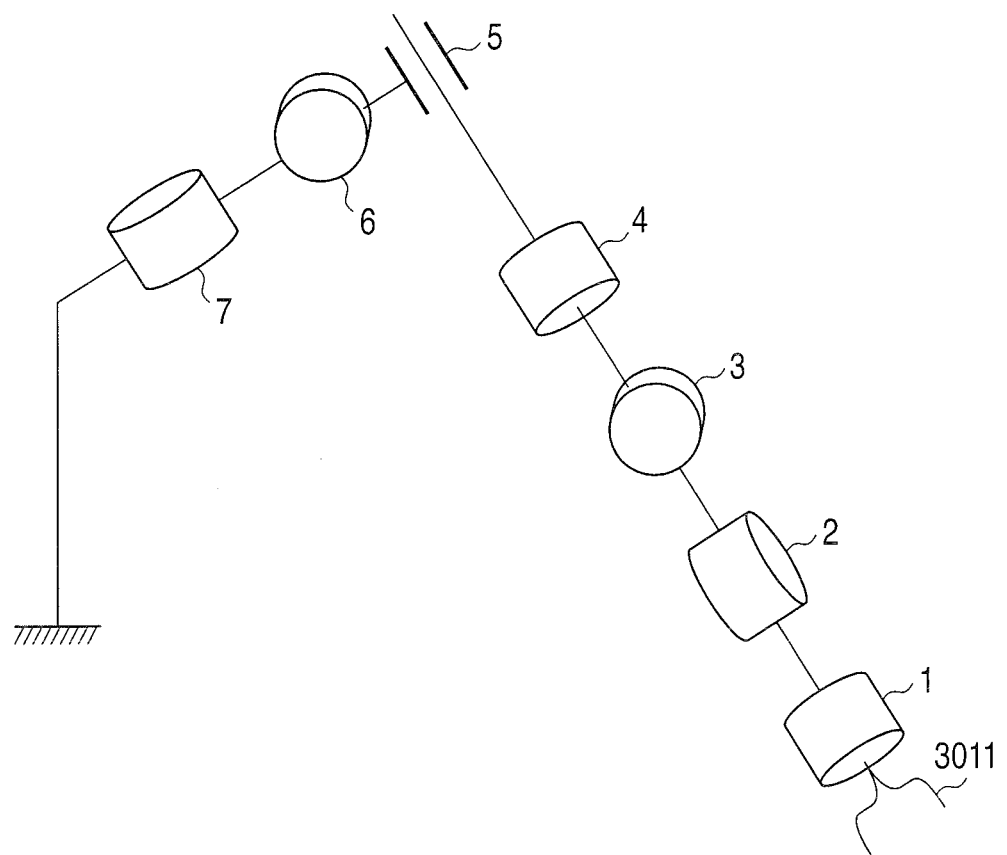
FIG. 3 is a diagram showing an example of a configuration of a slave manipulator.

The slave arm 301 includes the joints corresponding to 7 degrees of freedom, and the joints thereof are driven in accordance with control signals from the manipulator control unit 202. FIG. 3 is a diagram showing an example of a configuration of the slave arm 301. The slave arm 301 shown in FIG. 3 includes seven joints 1 to 7 which are disposed consecutively, and an end effector 3011 is attached to the leading end of the slave arm 301. In FIG. 3, the end effector 3011 is a gripper for example. As another example, a camera (electronic endoscope) or the like may be attached to the leading end.

Among the joints shown in FIG. 3, the joints 1 and 4 rotate about a roll axis; the joints 2 and 7 rotate about a yaw axis; and the joints 3 and 6 rotate about a pitch axis. The roll axis corresponds to an Xm axis of the master shown in FIG. 4C. The yaw axis corresponds to a Zm axis of the master shown in FIG. 4G. The pitch axis corresponds to a Ym axis of the master shown in FIG. 4C. The joint 5 is able to move along the roll axis. In the example of FIG. 3, all of the seven joints are independent from one another. Particularly, shown in FIG. 3 is the example in which the adjacent joints are operated corresponding to the different driven axes.

It is possible to realize 3 degrees of freedom of the position and 3 degrees of freedom of the orientation of the leading end in the slave arm 301 by driving the joints 2 to 7 shown in FIG. 3 in cooperation. Also, in addition to the joints, the joint 1 which causes rolling of the end effector 3011 is provided as a redundant joint. With such configuration, it is possible to appropriately select whether to cause rolling of the joint 4 which is distant from the leading end or to cause rolling of the joint 1 which is close to the leading end in the case of rolling the slave arm 301. In the embodiment, the inverse kinematic calculation is simplified by preventing the joint 1 and the joint 4 from being simultaneously driven.

The surgical table 302 is a table on which a patient 20 is laid, and the slave arm 301 is installed on the surgical table 302, for example.

Hereinafter, an operation of the master-slave manipulator of the embodiment will be described. The driven axes forming the manipulation unit 101 are driven when the operator 10 holding the remote manipulation device 100 moves or rotates the manipulation unit 101 or operates the gripper unit 1011 in a state of gripping the gripper unit 1011 provided in the manipulation unit 101 of the remote manipulation device 100. When the driven axes are driven, the driving amounts are detected by the position detectors (not shown). Detection signals (manipulation signals) of the position detectors are output to the control device 200. The manipulation signals are output at every predetermined time period of $\Delta t$.

The master control unit 201 of the control device 200 calculates command values of a position and an orientation of the leading end of the slave arm 301 in accordance with the manipulation signals corresponding to 6 degrees of freedom from the remote manipulation device 100. Also, the master control unit 201 selects one of the joints which are in redundancy relationship among the joints of the slave arm 301 as the driven joint and the remaining joints as fixed joints in accordance with the manipulation signals from the remote manipulation device 100. The master control unit 201 outputs a joint selection signal indicating the result of selection to the manipulator control unit 202 together with the command values for position and orientation.

Hereinafter, the joint selection signal will be described. As shown in FIG. 3, the slave arm 301 exemplified in the embodiment includes the joints corresponding to 6 degrees of freedom and the roll axis joint capable of driving independently from the other joints as the redundant joint. With such configuration, the slave arm 301 performs the driving corresponding to 7 degrees of freedom. In the case of executing the inverse kinematic calculation for obtaining driving amounts of the joints of the slave arm 301 from the command values of position and orientation of the leading end of the slave arm 301, it is possible to uniquely decide the driving amounts of the joints by the inverse kinematic calculation when the number of command values and the number of driven joints of the slave arm 301 are identical to each other. Therefore, the calculation is not complicated so much. In contrast, when the number of the driven joints of the slave arm 301 is larger than the number of the command values of the remote manipulation device 100, it is impossible to uniquely decide the driving amounts of the joints without performing a convergence calculation. Therefore, the calculation is complicated. In the embodiment, the inverse kinematic calculation is executed by setting one of the joint 1 (Roll 2) which is the redundant joint and the joint 4 (Roll 1) which is in redundancy relationship with the joint 1 as the fixed joint and the other as the driven joint. Thus, it is possible to consider the slave arm 301 having 7 degrees of freedom substantially as the slave arm 301 having 6 degrees of freedom in the inverse kinematic calculation. Therefore, it is possible to reduce the load imposed on the inverse kinematic calculation. The joint selection signal is a signal for distinguishing between the driven joint and the fixed joint from each other in the manipulator control unit 202.

The decision for setting either one of Roll 1 and Roll 2 as the fixed joint is made according to orientation changes of the remote manipulation device 100 at the predetermined intervals. Hereinafter, the idea will be described.

The orientation change of the remote manipulation device 100 is defined as described below. For example, a position of the manipulation unit 101 of the remote manipulation device 100 is at a position $O_m(t)$ at a certain time t as shown in FIG. 4A. Also, an orientation of the manipulation unit 101 at the time t is an orientation at which a master roll axis $X_m$, a master pitch axis $Y_m$, and a master yaw axis $Z_m$ are oriented to $X_m(t)$, $Y_m(t)$, and $Z_m(t)$ shown in FIG. 4A, respectively. From this state, the position of the manipulation unit 101 is assumed to have been changed to a position $O_m(t+1)$ shown in FIG. 4A at a time t+1 when the predetermined time Δt has elapsed. Also, the orientation of the manipulation unit 101 is assumed to have been changed to an orientation at which the master roll axis $X_m$, the master pitch axis $Y_m$, and the master yaw axis $Z_m$ are oriented to $X_m(t+1)$, $Y_m(t+1)$, and $Z_m(t+1)$ shown in FIG. 4A, respectively, at the time t+1. The orientation change of the manipulation unit 101 in the above-described case is obtained by synthesizing a rotation about the master roll axis $X_m(t)$, a rotation about the master pitch axis $Y_m(t)$, and a rotation about the master yaw axis $Z_m(t)$. Also, in mathematical terms, it is possible to replace the three rotations about the axes with a rotation about one axis. In other words, when a certain rotation axis $V_r(t)$ is set as shown in FIG. 4B, the orientation change of the manipulation unit 101 from the time t to the time t+1 is equivalent to a rotation of the manipulation unit 101 about the rotation axis $V_r(t)$ by a rotation amount θ(t). In general, a vector representing the rotation axis $V_r(t)$ is called equivalent rotation vector (also called equivalent rotation axis vector or the like). In the embodiment, the orientation change of the manipulation unit 101 is determined by using the equivalent rotation vector.

Hereinafter, a case of performing an operation of rolling the leading end of the slave arm 301 will be discussed. For example, it is necessary to perform a suturing motion for postoperative suturing in the endoscopic operation. In the suturing motion, the suturing of a required site of the patient 20 is performed by rolling the gripper which is the end effector 3011 attached to the leading end of the slave arm 301. As described in the foregoing, the slave arm 301 controls the position and the orientation of the end effector 3011 while operating the seven joints in cooperation. Here, when Roll 1 which is distant from the end effector 3011 is rolled, the rolling of the end effector 3011 is executed, but other joints can also be operated due to the rolling, thereby causing collision of the joints of the slave arm 301 with a circumjacent organ or the like in some cases.

Therefore, in the case where mainly the rolling operation, which is the rotation about the master roll axis $X_m(t)$, is required as in the suturing motion, it is desirable to cause rolling of Roll 2 which is the joint close to the leading end of the slave arm 301 in order to prevent unnecessary operation of other joints. In this case, is not particularly problematic to use Roll 1 as the fixed joint. By using Roll 1 as the fixed joint, it is possible to simplify the inverse kinematic calculation. However, when Roll 1 is used as the fixed joint, a range of position and orientation of the leading end of the slave arm 301 is greatly limited. Therefore, it is desirable to cause rolling of Roll 1 in the case where an operation also requires a rotation other than the rolling. In this case, it is not particularly problematic to use Roll 2 as the fixed joint. By using Roll 2 as the fixed joint, it is possible to simplify the inverse kinematic calculation.

It is possible to determine whether or not the command for mainly operating the roll axis joint at the leading end by the operation of the manipulation unit 101 is given depending on an angle φ(t) formed between the equivalent rotation vector $V_r(t)$ and the master roll axis $X_m(t)$ shown in FIG. 4C. When the equivalent rotation vector $V_r(t)$ and the master roll axis $X_m(t)$ are identical to each other (φ(t)=0), the orientation change of the manipulation unit 101 from the time t to the time t+1 is considered to be a orientation change by the rolling alone. In this case, it is possible to consider that a command for an operation which requires only the rolling of the leading end of the slave arm 301 is given from the manipulation unit 101. Actually, not only the case in which the equivalent rotation vector $V_r(t)$ and the master roll axis $X_m(t)$ are perfectly identical to each other, but also the case in which the rolling operation of the leading end is mainly performed though other operations may be included is taken into consideration. Therefore, a predetermined value is set for an angle φ(t) formed by the equivalent rotation vector $V_r(t)$ and the master roll axis $X_m(t)$, and it is considered that the operation for mainly moving the roll axis joint at the leading end is performed when φ(t) is equal to or below the predetermined value.

Figure 5:
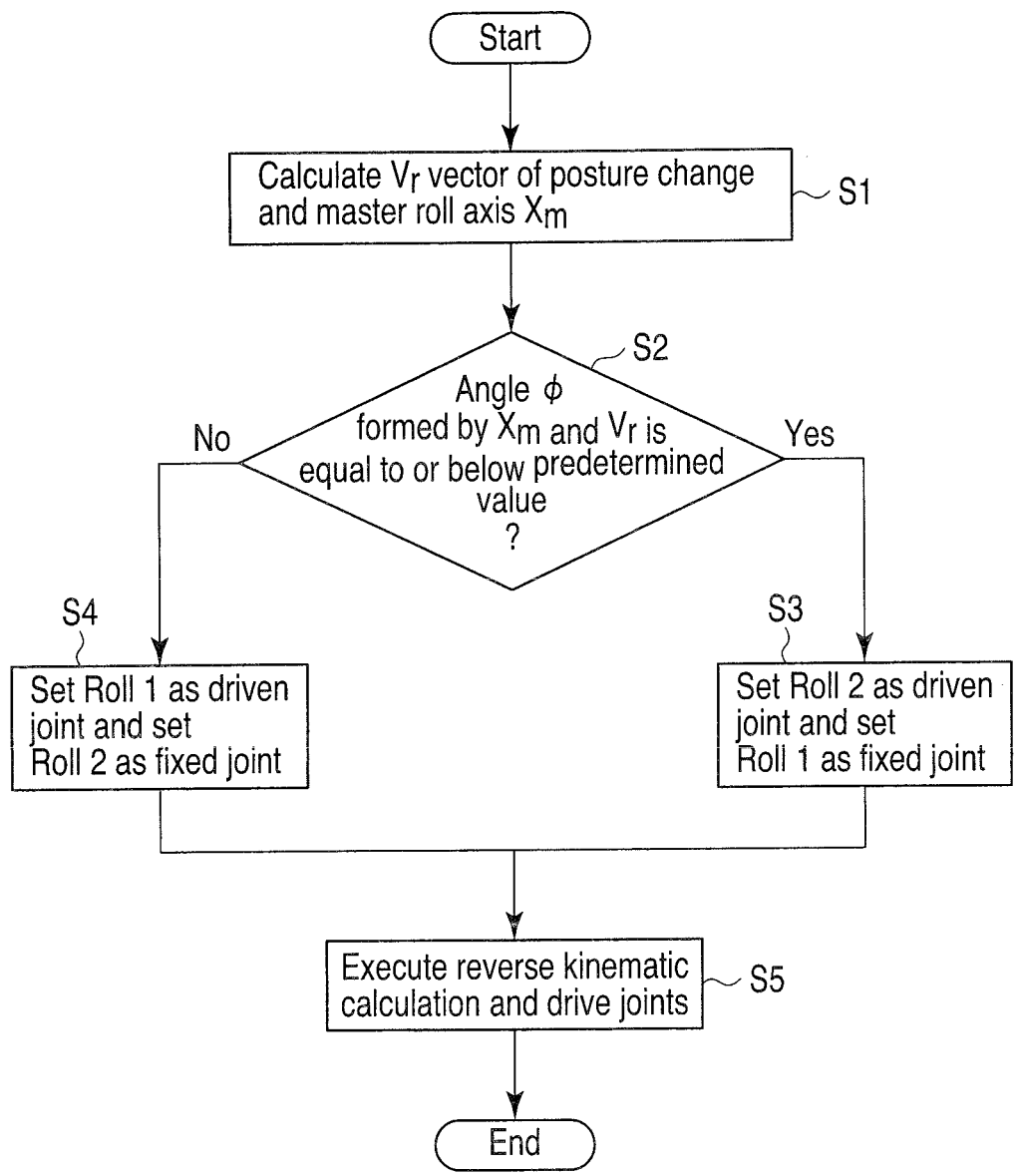
FIG. 5 is a flowchart showing an operation of a master-slave manipulator according to the embodiment of the invention.

FIG. 5 is a flowchart showing a flow of a drive control of the slave arm 301 in accordance with the above-described idea. The processing of FIG. 5 is executed at every predetermined time period of Δt. In the processing of FIG. 5, when the manipulation signals are input from the remote manipulation device 100, the master control unit 201 calculates, from the input signals, an equivalent rotation vector $V_r(t)$ representing an orientation change from a time t to a time t+1 and a master roll axis $X_m(t)$ at the time t (Step S1).

After the calculation of the equivalent rotation vector $V_r(t)$ and the master roll axis $X_m(t)$, the master control unit 201 determines whether or not an angle φ formed by $V_r(t)$ and $X_m(t)$ is equal to or below the predetermined value (Step S2). In the case where it is determined in Step S2 that the angle φ is equal to or below the predetermined value, i.e. that $V_r(t)$ and $X_m(t)$ are substantially identical to each other, the master control unit 201 sets the joint (Roll 2) to which the end effector 3011 is attached as a driven joint and the joint (Roll 1) which is in redundancy relationship with the joint (Roll 2) as a fixed joint (Step S3). In the case where the angle φ exceeds the predetermined value in the determination of Step S2, the master control unit 201 sets the joint (Roll 2) to which the end effector 3011 is attached as a fixed joint and the joint (Roll 1) which is in redundancy relationship with the joint (Roll 2) as a driven joint (Step S4).

After setting each of Roll 1 and Roll 2 to be used as the driven joint or the fixed joint, the master control unit 201 sends to the manipulator control unit 202 command values for instructing a position and an orientation of the leading end of the slave arm 301 and joint selection signal indicating that each of Roll 1 and Roll 2 is set as the driven joint or the fixed joint. Upon reception of the command values and signal, the manipulator control unit 202 calculates driving amounts of the joints of the slave arm 301 by executing an inverse kinematic calculation in a state where Roll 1 or Roll 2 is set as the fixed joint. The joint set as the fixed joint is excluded from the joints in the calculation. The manipulator control unit 202 drives the joints of the slave arm 301 in accordance with the calculated driving amounts (Step S5). As the inverse kinematic calculation, known various methods such as an analytic method may be employed. Details of the methods are omitted herein.

As described above, according to the embodiment, it is determined whether or not the instruction for the operation mainly requiring rolling such as the suturing motion is given based on the orientation change of the manipulation unit 101 of the remote manipulation device 100, in the slave arm 301 including the joint Roll 2 as the redundant joint for rolling the end effector 3011 in addition to the joint for rolling the slave arm 301. As a result of the determination, in the case where it is determined that the instruction for causing the operation mainly requiring rolling is given (in the case where the equivalent rotation vector $V_r(t)$ and the master roll axis $X_m(t)$ are substantially identical to each other), the inverse kinematic calculation is performed by setting Roll 2 as the driven joint and Roll 1 as the fixed joint. On the other leading end, in the case where it is determined that the instruction for causing the operation requiring orientation change other than rolling is given (in the case where the equivalent rotation vector $V_r(t)$ and the master roll axis $X_m(t)$ are not substantially identical to each other), the inverse kinematic calculation is performed by setting Roll 1 as the driven joint and Roll 2 as the fixed joint. As described above, in the embodiment, Roll 1 and Roll 2 are selectively used depending on the orientation change per predetermined time of the manipulation unit 101. With such configuration, even in the case where the remote manipulation device and the slave arm are different from each other in configuration, it is possible to reduce a load to be imposed on the inverse kinematic calculation while reflecting intention of the operation by the operator 10. Also, it is possible to automatically perform the selective use of Roll 1 and Roll 2 in the embodiment. With such configuration, since it is not necessary to change the driven joint by using a switch, it is possible to reduce a labor of the operator 10.

Further, the orientation change of the manipulation unit 101 is represented by the equivalent rotation vector $V_r(t)$ in the embodiment. Therefore, it is possible to appropriately detect the orientation change of the manipulation unit 101 of remote manipulation devices 100 of various types of configurations.

The remote manipulation device 100 which includes the manipulation unit 101 having the 6 degrees of freedom (3 degrees of freedom for position, 3 degrees of freedom for orientation) and the slave arm 301 having the 7 degrees of freedom (3 degrees of freedom for position, 3 degrees of freedom for orientation, rolling of the leading end) has been described in the above-describe example. However, the relationship between the degree of freedom of the manipulation unit 101 of the remote manipulation device 100 and the degree of freedom of the slave arm 301 is not limited to the above-described example. For example, the above-described technology of the embodiment is applicable to the case of eliminating the degree of freedom for position. The case of eliminating the degree of freedom for position means the case in which the manipulation unit 101 has 3 degrees of freedom, and the slave arm 301 has 4 degrees of freedom. Further, though the number of the redundant joints is one in the above-described example, the number of the redundant joints is not limited to one. For example, the technology of the embodiment is applicable to the case in which another roll axis joint is provided between the joint 2 and the joint 3 in FIG. 3. In this case, the joint provided between the joint 2 and the joint 3 is continuously set as the driven joint.

Figure 6A:
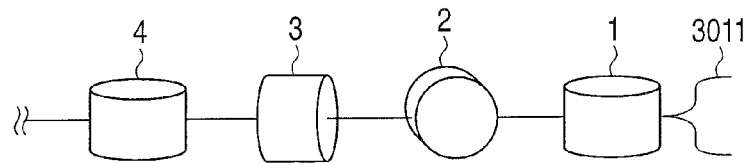
FIGS. 6A and 6B are diagrams showing a modification example in which a redundant joint is a yaw axis joint.
Figure 6B:
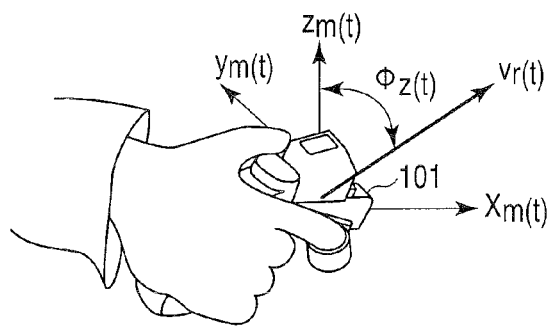
Figure 7A:
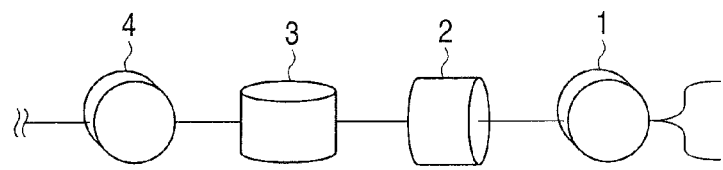
FIGS. 7A and 7B are diagrams showing another modification example in which a redundant joint is a pitch axis joint.
Figure 7B:
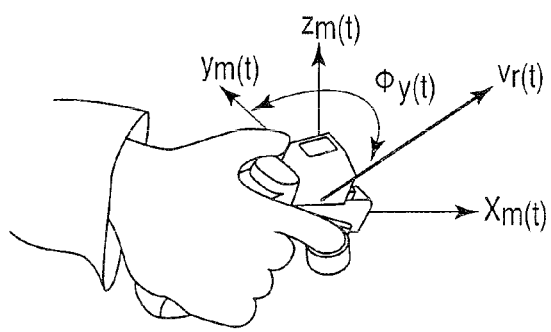

Also, in the example of FIG. 3, the redundant joint to which the end effector 3011 is attached is used as the roll axis joint. However, the above-described technology of the embodiment is applicable to a configuration in which the end effector 3011 is attached to the yaw axis joint as shown in FIG. 6A and the configuration in which the end effector 3011 is attached to the pitch axis joint as shown in FIG. 7A. In the case of the configuration of FIG. 6A, it is determined whether an angle $\phi_z(t)$ formed by the equivalent rotation vector $V_r(t)$ and the master yaw axis $Z_m(t)$ ($\phi_z(t)$ is shown in FIG. 6B) is equal to or below a predetermined value in the determination of Step S2, and the joint (the joint 1 in FIG. 6A) close to the end effector 3011 is set as the driven joint in the case where the angle $\phi_z(t)$ is equal to or below the predetermined value. Also, in the case of the configuration of FIG. 7A, it is determined whether an angle $\phi_y(t)$ formed by the equivalent rotation vector $V_r(t)$ and the master pitch axis $Y_m(t)$ ($\phi_y(t)$ is shown in FIG. 7B) is equal to or below a predetermined value in the determination of Step S2, and the joint (the joint 1 in FIG. 7A) close to the end effector 3011 is set as the driven joint in the case where the angle $\phi_y(t)$ is equal to or below the predetermined value. As described above, since the selection of the redundant joint and the joint in redundancy relationship with the redundant joint in the embodiment is determined based on the angle formed by the equivalent rotation vector representing the orientation change of the remote manipulation device 100 and the axis of the remote manipulation device 100 which is preliminarily set depending on the slave arm 301, it is possible to perform the selection in accordance with slave arms 301 of various types of configurations.

In the case where the joint 2 is rotated by 90 degrees in the example of FIGS. 7A and 7B, the joint 1 is equivalent to the yaw axis joint. In this case, it is possible to perform the determination of Step S2 between the joint 1 and the joint 3. Thus, the determination of Step S2 is performed not only between the joints which have the parallel rotation axes in the initial state, but also between the joints in which the rotation axes become parallel to each other during driving in the mechanism having the redundant degree of freedom.

Figure 8:
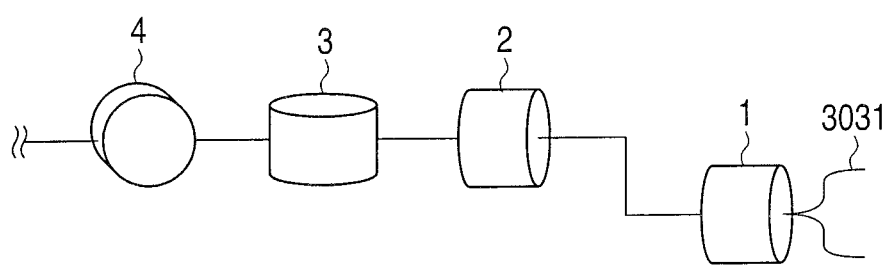
FIG. 8 is a diagram showing an example of a configuration of a slave arm in which joints in redundancy relationship are disposed adjacent to each other and capable of being independently driven.

Also, in the above-described examples, the slave arm 301 having the following configuration is described. That is, the joint which is in the independent relationship with the joints having the parallel rotation axes and in the redundancy relationship is disposed between these joints with the rotation axis intersecting the joints. Actually, the joints in the redundancy relationship may be disposed adjacent to each other as long as the joints forming the slave arm 301 are independently driven. For example, the above-described technology of the embodiment is applicable to the joint 1 and the joint 2 of the configuration shown in FIG. 8.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A master-slave manipulator comprising:
a remote manipulation device as a master which gives an operating command corresponding to a plurality of degrees of freedom;
a slave manipulator which includes a plurality of joints corresponding to the degrees of freedom and includes a redundant joint among the joints; and
a control unit which controls operations of the joints in accordance with the operating command, wherein
the control unit calculates an orientation change of the remote manipulation device from the operating command at predetermined time intervals and selects and drives one of the joints in redundancy relationship among the joints in accordance with the orientation change, and
the control unit selects and drives one of the joints in redundancy relationship among the joints based on an angle formed by an axis representing the orientation change and a predetermined axis of the remote manipulation device.

2. The master-slave manipulator according to claim 1, wherein the axis representing the orientation change corresponds to a rotation axis in a case where the orientation change is a rotation from before the orientation change to after the orientation change.

3. The master-slave manipulator according to claim 2, wherein a joint having a rotation axis orthogonal to the axes of the joints in redundancy relationship exists between the joints.

4. The master-slave manipulator according to claim 2, wherein the joints in redundancy relationship are disposed adjacent to each other.

5. The master-slave manipulator according to claim 2, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

6. The master-slave manipulator according to claim 3, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

7. The master-slave manipulator according to claim 4, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

8. The master-slave manipulator according to claim 1, wherein a joint having a rotation axis orthogonal to the axes of the joints in redundancy relationship exists between the joints.

9. The master-slave manipulator according to claim 8, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

10. The master-slave manipulator according to claim 1, wherein the joints in redundancy relationship are disposed adjacent to each other.

11. The master-slave manipulator according to claim 10, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

12. The master-slave manipulator according to claim 1, wherein the control unit selects and drives the joint closest to a leading end of the slave manipulator among the joints in redundancy relationship in a case where the angle formed by the axis representing the orientation change and the predetermined axis of the remote manipulation device is equal to or below a predetermined value, and selects and drives the joint most distant from the leading end of the slave manipulator among the joints in redundancy relationship in a case where the angle formed by the axis representing the orientation change and the predetermined axis of the remote manipulation device exceeds the predetermined value.

13. The master-slave manipulator according to claim 1, wherein the control unit sets, as a fixed joint, the joint which is not selected from the joints in redundancy relationship among the joints and calculates driving amounts of the remaining joints by an inverse kinematic calculation.

\* \* \* \* \*